(12) United States Patent
Koay et al.

(10) Patent No.: US 9,277,947 B2
(45) Date of Patent: Mar. 8, 2016

(54) VARIABLE ANGLE BONE FIXATION DEVICE

(71) Applicant: DePuy Synthes Products, Inc., Raynham, MA (US)

(72) Inventors: Kenny Koay, West Chester, PA (US); Rod McMillan, West Chester, PA (US); Kenneth Kobayashi, West Chester, PA (US); Rene Haag, West Chester, PA (US); Robert Limouze, West Chester, PA (US); Mike Wahl, West Chester, PA (US); Mirko Rocci, Solothurn (CH)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 0 days.

(21) Appl. No.: 14/662,895

(22) Filed: Mar. 19, 2015

(65) Prior Publication Data
US 2015/0190185 A1    Jul. 9, 2015

Related U.S. Application Data

(63) Continuation of application No. 13/534,831, filed on Jun. 27, 2012.

(51) Int. Cl.
*A61B 17/80* (2006.01)
*A61B 17/86* (2006.01)
*A61B 17/84* (2006.01)

(52) U.S. Cl.
CPC ........ *A61B 17/8057* (2013.01); *A61B 17/8052* (2013.01); *A61B 17/84* (2013.01); *A61B 17/86* (2013.01); *A61B 17/863* (2013.01); *A61B 17/8605* (2013.01); *A61B 17/866* (2013.01); *A61B 17/8615* (2013.01); *A61B 17/8635* (2013.01); *A61B 2017/8655* (2013.01)

(58) Field of Classification Search
CPC ........ A61B 17/56; A61B 17/58; A61B 17/68; A61B 17/80; A61B 17/8052; A61B 17/8057; A61B 17/84; A61B 17/86; A61B 2017/8655; A61B 17/866; A61B 17/88
See application file for complete search history.

(56) References Cited

U.S. PATENT DOCUMENTS

| | | | |
|---|---|---|---|
| 5,556,483 | A | 9/1996 | Tahara et al. |
| 5,593,510 | A | 1/1997 | Tahara et al. |
| 5,733,287 | A | 3/1998 | Tepic et al. |
| 5,792,282 | A | 8/1998 | Tahara et al. |
| 6,165,597 | A | 12/2000 | Williams et al. |

(Continued)

FOREIGN PATENT DOCUMENTS

WO    2011/154891    12/2011

OTHER PUBLICATIONS

"Cyprus Anterior Cervical Plate System", Sutgical Technique, Biomet Spine, 2008, 24 sheets.

(Continued)

*Primary Examiner* — Larry E Waggle, Jr.
(74) *Attorney, Agent, or Firm* — Fay Kaplun & Marcin, LLP

(57) ABSTRACT

A bone fixation element includes a threaded head and a shaft extending along a longitudinal axis from a proximal end to a distal end, an outer surface of the head being one of carburized and nitrided and including a first groove extending into an outer surface of the head along a path interrupting the threading and extending along an angle counter to an angle of the threading.

18 Claims, 5 Drawing Sheets

(56) References Cited

U.S. PATENT DOCUMENTS

| | | | |
|---|---|---|---|
| 6,206,881 B1 | 3/2001 | Frigg et al. | |
| 6,322,562 B1 | 11/2001 | Wolter | |
| 6,461,448 B1 | 10/2002 | Williams et al. | |
| 7,648,588 B2 | 1/2010 | Hammond et al. | |
| 7,695,502 B2 | 4/2010 | Orbay et al. | |
| 7,776,076 B2 | 8/2010 | Grady et al. | |
| 7,905,909 B2 * | 3/2011 | Orbay | A61B 17/8057 606/280 |
| 7,955,364 B2 | 6/2011 | Ziolo et al. | |
| 8,382,811 B2 | 2/2013 | Crook et al. | |
| 2007/0083207 A1 * | 4/2007 | Ziolo | A61B 17/8057 606/287 |
| 2007/0088360 A1 | 4/2007 | Orbay et al. | |
| 2008/0234749 A1 | 9/2008 | Forstein | |
| 2009/0018557 A1 | 1/2009 | Pisharodi | |
| 2009/0143825 A1 | 6/2009 | Graham et al. | |
| 2009/0292318 A1 | 11/2009 | White et al. | |
| 2010/0016858 A1 | 1/2010 | Michel | |
| 2010/0094357 A1 | 4/2010 | Wallenstein et al. | |
| 2010/0100134 A1 | 4/2010 | Mocanu | |
| 2010/0168841 A1 * | 7/2010 | Furst | A61L 27/047 623/1.42 |
| 2011/0022173 A1 | 1/2011 | Melkent et al. | |
| 2011/0077732 A1 | 3/2011 | Bayer et al. | |
| 2011/0106172 A1 | 5/2011 | Wallenstein et al. | |
| 2011/0118795 A1 | 5/2011 | Hashmi et al. | |
| 2011/0224671 A1 | 9/2011 | Koay et al. | |
| 2011/0238122 A1 | 9/2011 | Gradl | |

OTHER PUBLICATIONS

"Forerunner plating System", Featuring SphereLock Technology, Biomet Trauma, 2010, 27 sheets.

* cited by examiner

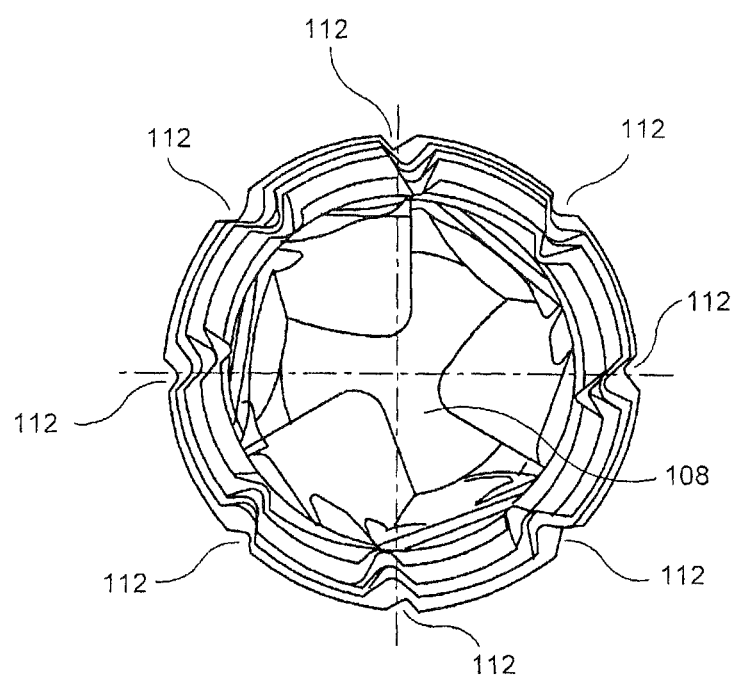
F I G. 6

VARIABLE ANGLE BONE FIXATION DEVICE

PRIORITY CLAIM

The present application is a Continuation Application of pending U.S. patent application Ser. No. 13/534,831 filed on Jun. 27, 2012. The disclosure of the above application is incorporated herein by reference.

BACKGROUND

Bone fixation plates are often positioned over a fractured or otherwise damaged portion of bone and secured thereto using bone screws inserted through screw holes of the bone fixation plate. The screw holes extend transversely through the bone plate and are sometimes formed with threads to lockingly engage a threaded head of the bone screw. Variable angle screws are often employed which permit a user to insert the screw through the plate at a user-selected angle relative to an axis of the plate hole. However, the engagement threads of the head of such variable angle screw heads with the threading of the plate hole may burr threads of one or both of the bone screw and the bone plate, causing a loss in bone fixation strength. Damage to the bone plate or bone screw in this manner may cause the bone fixation procedure to lose efficacy. Those skilled in the art continue to search for ways to increase the strength of the screw-plate interface in variable angle systems.

SUMMARY OF THE INVENTION

The present invention is directed to a bone fixation element comprising a threaded head and a shaft extending along a longitudinal axis from a proximal end to a distal end, an outer surface of the head being one of carburized and nitrided and including a first groove extending into an outer surface of the head along a path interrupting the threading and extending along an angle counter to an angle of the threading.

BRIEF DESCRIPTION OF THE DRAWINGS

FIG. 6 shows a perspective view of a bone fixation element according to an alternate embodiment of the present invention;

DETAILED DESCRIPTION

Figure 1:
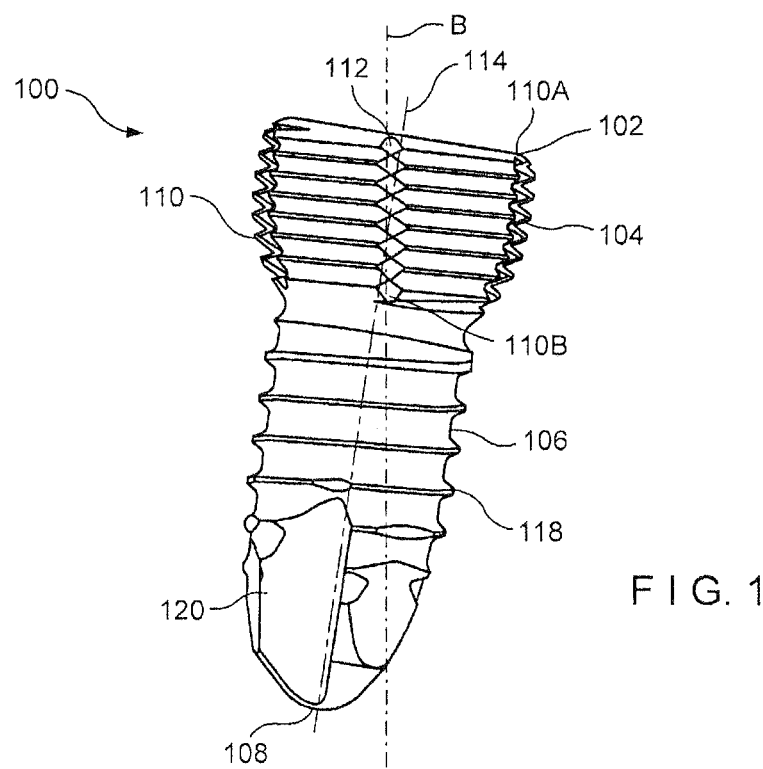
FIG. 1 shows a first perspective view of a bone fixation element according to an exemplary embodiment of the present invention.
Figure 2:
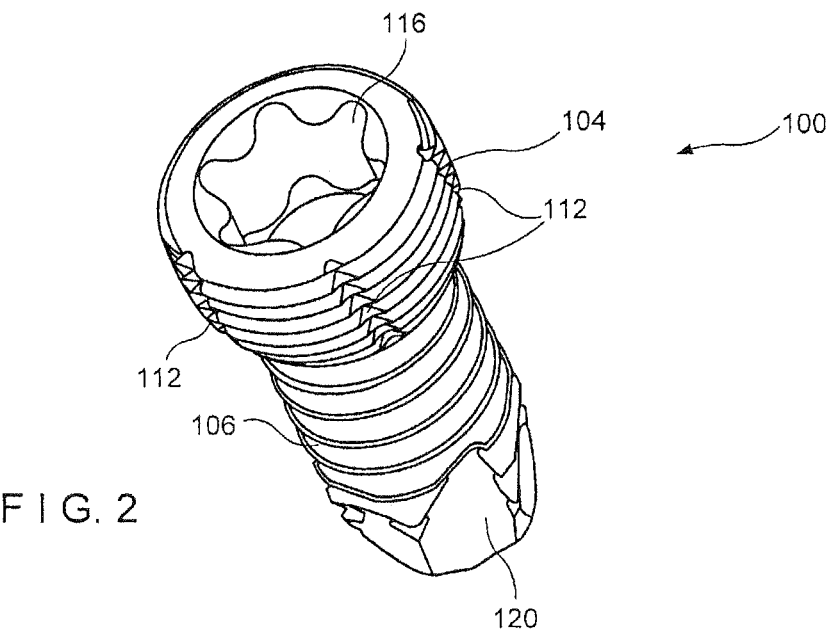
FIG. 2 shows a second perspective view of the bone fixation element of FIG. 1.
Figure 3:
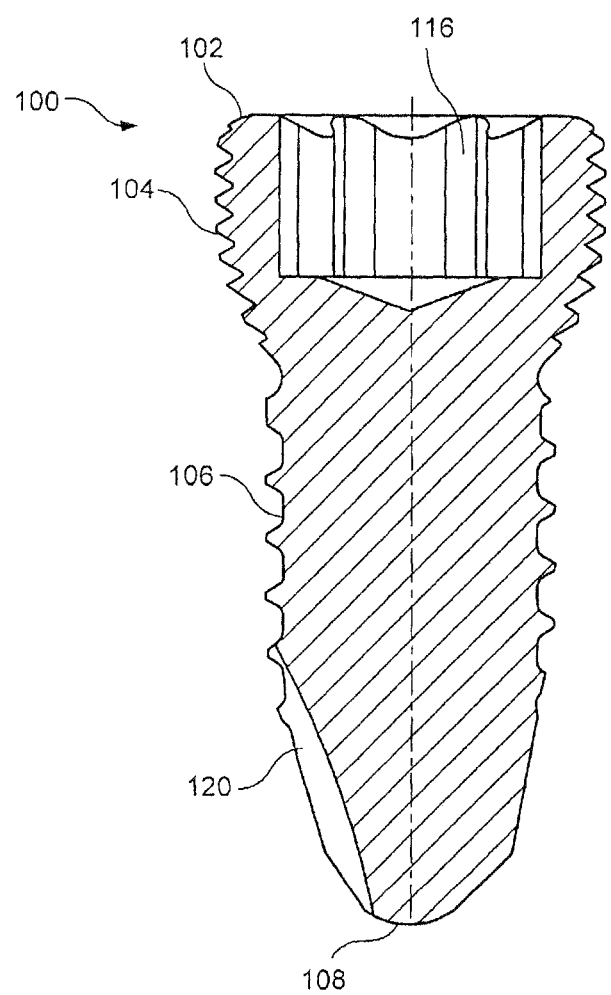
FIG. 3 shows a partial cross-sectional view of the bone fixation element of FIG. 1.
Figure 4:
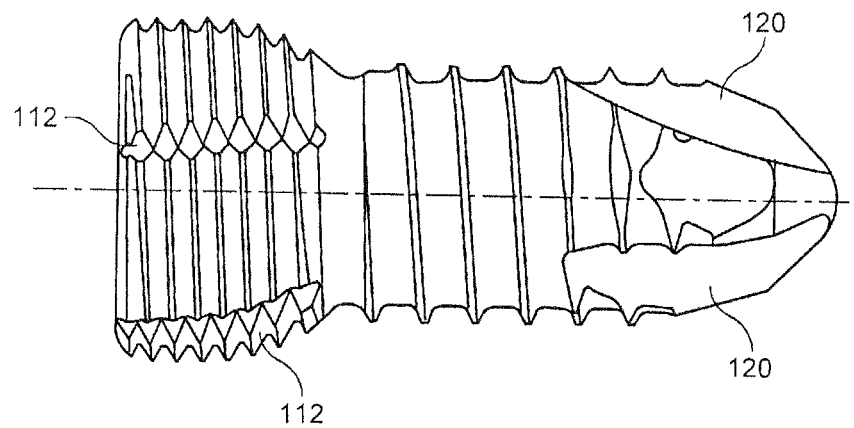
FIG. 4 shows a third perspective view of the bone fixation element of FIG. 1.

The present invention may be further understood with reference to the following description and the appended drawings, wherein like elements are referred to with the same reference numerals. The present invention relates to the stabilization of bones and, in particular, to the stabilization of a fractured or otherwise damaged bone using a bone screw inserted through a bone fixation device (e.g., a bone plate). Exemplary embodiments of the present invention describe a variable angle bone screw having a threaded head and a threaded shaft and having a carburized or nitrided outer surface configured to increase a surface hardness thereof to a desired level. The threaded head comprises one or more grooves extending into an outer surface thereof at an angle relative to a longitudinal axis of the bone screw to aid in alignment of the threads of the head with threads of a variable angle screw hole of the bone fixation device. The shaft comprises one or more notches extending into an outer surface thereof at any angle relative to the longitudinal axis within a permitted range of angulation, as will be described in greater detail later on. In one embodiment, the bone plate may be formed of a metallic alloy exhibiting a hardness within a predetermined range. The bone screw may be carburized or nitrided such that an outer surface of the bone screw has a hardness greater than a hardness of the bone plate. Thus, the exemplary bone screw according to the invention prevents burring of the screw during insertion into the bone plate while providing a consistent connection strength to the bone and bone plate. Furthermore, the exemplary system according to the invention reduces galling during use while also providing an increased overall strength when compared to standard screws including increased yield strength, ultimate tensile strength and fatigue strength, as those skilled in the art will understand. It should be noted that the terms "proximal" and "distal" as used herein, are intended to refer to a direction toward (proximal) and away from (distal) a user of the device.

As shown in FIGS. 1-6, a bone screw 100 according to an exemplary embodiment of the invention extends from a proximal end 102 comprising a head 104 along an elongated shaft 106 to a distal end 108. In an exemplary embodiment, an outer surface of the head 104 is substantially spherical to permit variable angle insertion of the bone screw 100 into a bone fixation device 200, as will be described in greater detail later on. It is noted, however, that the head 104 may be formed in any other shape without deviating from the scope of the invention (e.g., to permit a single-angle insertion of the bone screw 100 into the bone fixation device 200). The outer surface of the head 104 is provided with threading 110 having a pitch configured to lockingly engage threading 212 formed on a walls of an opening 202 extending through the bone fixation device 200, as will also be described in greater detail later on. One or more grooves 112 may be provided on the head 104, each groove 112 extending at least partially into the threads 110 and extending along an axis substantially angled with respect to a longitudinal axis 114 of the bone screw 100. The grooves 112 are configured to interrupt the thread 110, thus creating a plurality of thread starts which aid in alignment of the thread 110 with the threads 212 of the hole 202 in an operative configuration especially when the bone screw 100 is inserted into a bone plate hole angled with respect to an axis of the bone plate hole (i.e., when the threading of the head 104 is misaligned with the threading of the bone plate hole). The grooves 112 further permit the bone screw 100 to advance distally into the bone when rotated via a driving mechanism (not shown).

Each of the grooves 112 may be angled, for example, at an angle of approximately 8.5±1° relative to the line B-B, although any other angle may be used without deviating from the scope of the invention. In an exemplary embodiment, the grooves 112 are angled counter to a direction of the threading 110. For example, as seen in FIG. 1, the line B-B is perpendicular to the path of the threading 110 and the groove 112 is angled relative to the line B-B so that, traveling along the threading 110 from a proximal end 110A thereof toward a distal end 110B, the angle between the threading 110 and the groove 112 is greater than 90° on the proximal side of the thread and less than 90° on the distal side of the thread. In another embodiment, the grooves 112 extend at an angle of approximately 5-85° relative to the line B-B (i.e., 95° to 175° relative to the threading 110). In yet another embodiment, the grooves 112 may extend substantially parallel to the line B-B. The grooves 112 according to this embodiment extend along substantially a complete length of the threading 110. In another embodiment (not shown), the grooves 112 may extend for only a partial length of the threading 110.

Figure 5:
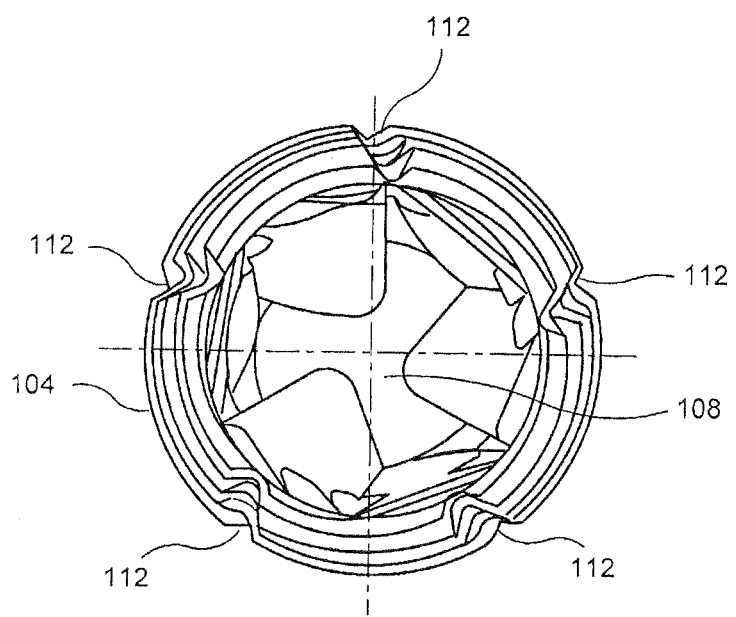
FIG. 5 shows a fourth perspective view of a head of the bone fixation element of FIG. 1.
Figure 7:
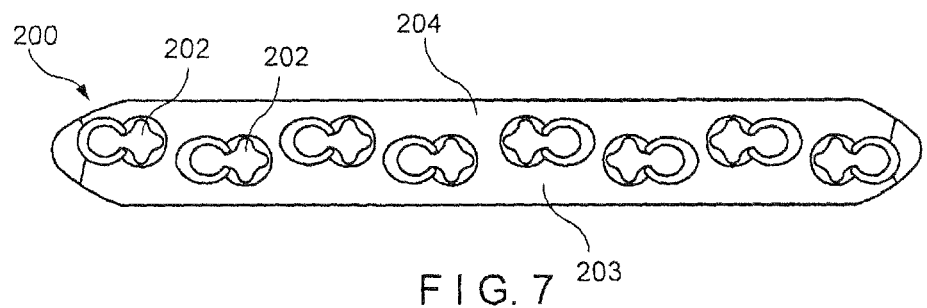
FIG. 7 shows a perspective view of a first surface of a bone plate according to the present invention.
Figure 8:
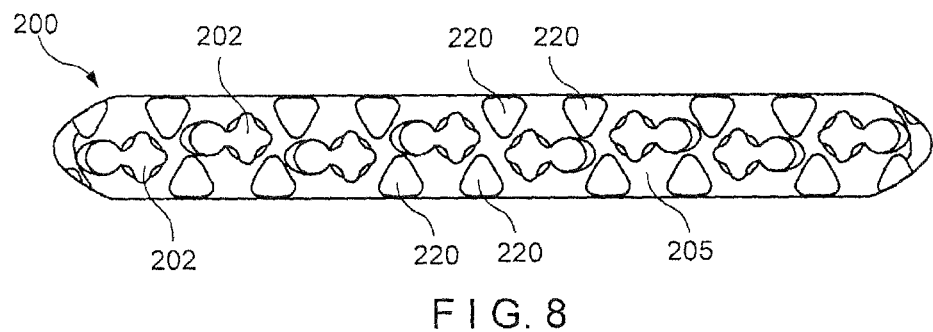
FIG. 8 shows a perspective view of a second surface of the bone plate of FIG. 7.
Figure 9:
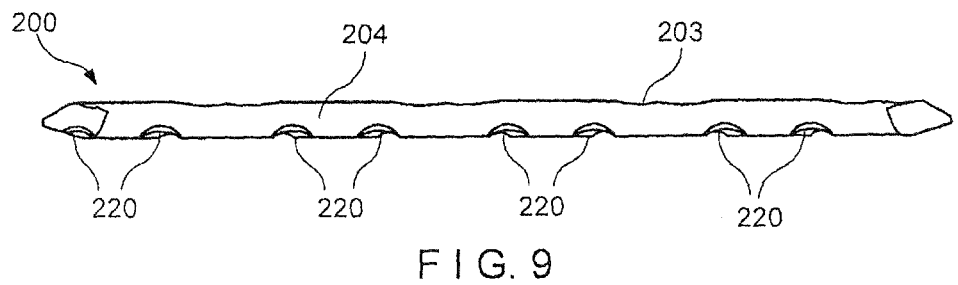
FIG. 9 shows a lateral view of the bone plate of FIG. 7.
Figure 10:
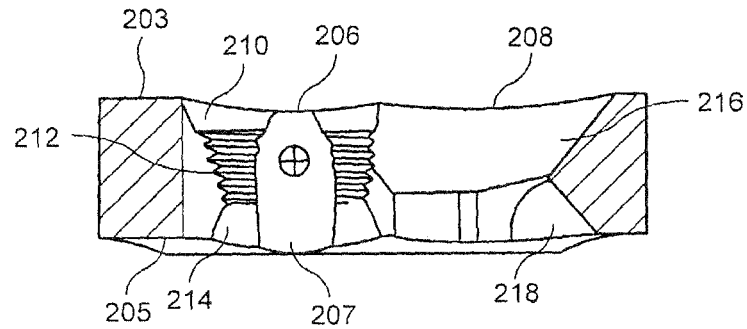
FIG. 10 shows a partial cross-sectional view of a plate hole of the bone plate of FIG. 7.

In a first exemplary embodiment of the invention, the bone screw 100 may be formed with five grooves 112 disposed evenly circumferentially about the head 104 and equidistant from one another, as shown in FIG. 5. Specifically, each of the grooves 112 in this embodiment is separated from adjacent grooves 112 by approximately 72°. In another embodiment (not shown), the bone screw 100 comprises six grooves 112 separated from one another by approximately 60°. In yet another embodiment, as shown in FIG. 6, the bone screw 100 may comprise eight grooves 112 separated from one another by approximately 45°.

The head 104 may further comprises a recess 116 extending thereinto from the proximal end 102. The recess 116 is configured to permit engagement with a distal end of a driving mechanism (not shown) for applying torque to the bone screw 100 as would be understood by those skilled in the art. The embodiment of FIGS. 1-6 is depicted with a torx-shaped recess 116. It is noted, however, that any other shape may be employed without deviating from the scope of the invention (e.g., slotted, phillips, square, hexagonal, etc.), as those skilled in the art would understand.

The shaft 106 is provided with threading 118 having a pitch substantially the same as the pitch of the threads 110. In another embodiment of the invention (not shown), the pitch of the threading 118 may be greater than or smaller than the pitch of the threads 110. The threading 118 of the shaft 106 may be formed with two leads, as those skilled in the art will understand. The multi-lead configuration of the threading 118 aids in linear advancement of the bone screw 100 into the bone, as those skilled in the art will understand. As would be understood by those skilled in the art, the length of the shaft 106 is generally selected to conform to requirements of a target procedure, A distal portion of the shaft 106 may comprise one or more notches 120 configured to create a gap in the continuity of the threads 110 and permit self-tapping of the bone screw 100, as those skilled in the art will understand. The distal portion of the shaft 106 may taper to a smaller diameter at the distal end 106 to, for example, aid in insertion. The distal end 106 may be sharpened or blunt as desired.

The bone screw 100 may be formed of a material selected to have a greater hardness that a material of a bone fixation device 200 with which it is to be employed. Specifically, the bone screw 100 may be formed of one of stainless steel and CCM (Co-28Cr-6Mo Alloy). The bone screw 100 may then be carburized or nitrided to further increase a surface hardness thereof to approximately 68 HRC or more, as those skilled in the art will understand. In an exemplary embodiment, the hardness of the bone screw 100 may be approximately 67-74 HRC and, more particularly, 67.5-70.3 HRC. In contrast, the bone fixation device 200 may be formed of commercially pure Titanium grades 1, 2, 3 and 4, Ti-6Al-7Nb, Ti-6Al-4V, Ti-6Al-4V ELI, Ti-15Mo, CCM (Co-28Cr-6Mo Alloy), stainless steel or another material different than the material of the bone screw 100. As those skilled in the art will understand, a hardness of the bone fixation device 200 may be between approximately 75 HRB (e.g., for a CP1 material) and approximately 45 HRC (e.g., for a CCM material). This configuration prevents burring of the threads 110 of the bone screw 100 as they are inserted into the bone fixation device 100 while also increasing a holding strength of the bone fixation system in the bone.

FIGS. 7-10 depict the exemplary bone fixation device 200 according to the invention. Although the device 200 shown is a bone plate, it is submitted that any other bone fixation device may be used without deviating from the scope of the invention (e.g., an intramedullary nail, etc.). The bone plate 200 may, for example, be a 4.5 mm broad variable angle compression plate including eight holes 202 extending through a body 204. Any or all of the holes 202 may be formed as variable angle combination holes comprising a first variable angle hole portion 206 and a second compression hole portion 208 open to the first hole portion. The first hole portion 206 may comprise a first relief cut 210 formed adjacent a first surface 203, a second cylindrical threaded portion 212 extending distally therefrom and a third relief cut 214 formed adjacent a second surface 205 configured to contact the bone in an operative configuration. The relief cut 210 may extend at an angle of approximately 15° relative to a longitudinal axis of the hole 202, although other angles may be used without deviating from the scope of the invention. The first hole portion 206 further comprises one or more slots 207 provided on an outer wall thereof, the slots 207 extending substantially perpendicular to a screw hole axis. As those skilled in the art will understand, the slots 207 interrupt the threads of the threaded portion 212 to provide multiple thread starts which aid in alignment of the threaded portion 212 with the bone screw 100. The second hole portion 208 may comprise a first tapered hole portion 216 and a second tapered hole portion 218 extending distally therefrom. It is noted that although the bone fixation device 200 is depicted with eight holes, any other number of holes may be used without deviating from the scope of the invention and these holes may include any variety of know bone screw mounting holes. The bone fixation device 200 may also comprise any number and combination of variable angle holes, single holes and combination holes without deviating from the scope of the invention. The second surface 205 may further comprise a plurality of undercuts 220 configured to reduce a contacting surface area between the bone fixation device 200 and the bone to, for example, reduce impairment of blood supply after implantation, as those skilled in the art will understand.

In an operative configuration, the bone screw 100 is inserted through the bone fixation device 200 and into the bone. As those skilled in the art will understand, a physician or other user may select a desired angle of insertion to conform to the requirements of a particular procedure. Multiple thread starts provided by the grooves 112 provided on the head 104 and the slots 207 provided in the hole 202 aid in alignment of the threads 110 of the head with the threaded portion 212 of the hole 202. As the bone screw 100 is screwed through the bone fixation device 200 and into the bone, the carburized or nitrided outer surface of the bone screw 100 prevents burring of the threads 110. The increased rigidity of the bone screw 100 relative to the bone fixation device 200 also permits removal and reinsertion of the bone screw 100 into the bone (e.g., to correct a position thereof within the bone) without causing a burring thereof.

It will be apparent to those skilled in the art that various modifications and variations can be made in the structure and the methodology of the present invention without departing from the spirit or scope of the invention. Thus, it is intended that the present invention cover the modifications and variations of this invention provided that they come within the scope of the appended claims and their equivalents.

What is claimed is:

1. A system for bone fixation, comprising:
a bone fixation plate defining a first surface configured to contact bone in an operative configuration and a second surface opposite the first surface, the bone fixation plate defining an opening that extends therethrough from the first surface to the second surface, the bone fixation plate having a first hardness; and
an elongated bone implant having a shaft configured for insertion through the opening of the bone fixation plate and into a bone, an outer surface of the bone implant being one of carburized and nitrided to have a second hardness that is greater than the first hardness,
wherein the first and second hardness are selected so that a difference therebetween increases a strength of an interface between the bone implant and the bone fixation plate and avoids burring of the bone implant when the bone implant is inserted through the opening of the bone fixation plate.

2. The system of claim 1, wherein the second hardness is in the range of 67-74 HRC.

3. The system of claim 1, wherein the bone implant is a bone screw having a threaded head.

4. The system of claim 1, wherein the opening is a variable angle hole.

5. The system of claim 1, wherein the first hardness is in the range of 74 HRB-44 HRC.

6. The system of claim 1, wherein the bone implant is formed of one of stainless steel and CCM.

7. The system of claim 1, wherein the bone fixation plate is formed of one or more of commercially pure Titanium grades 1, 2, 3 and 4, Ti-6Al-7Nb, Ti-6Al-4V, Ti-6Al-4V ELI, Ti-15Mo, CCM (Co-28Cr-6Mo Alloy) and stainless steel.

8. A bone fixation system, comprising:
a bone screw having a head and a shaft, the head having a proximal end, a distal end spaced from the proximal end in a distal direction, and an outer surface that extends from the distal end to the proximal end, wherein the outer surface of the head carries a thread that is sloped in the distal direction as it extends clockwise about the outer surface with respect to a view in the distal direction, the head further defining a groove that extends into the outer surface along a path that interrupts the thread, wherein the path is sloped counterclockwise as it extends in the distal direction with respect to the view in the distal direction, wherein the outer surface of the head is one of carburized and nitrided so that the head has a first hardness; and
an elongated bone plate that extends along a plate axis and defines a first surface configured to contact bone in an operative configuration, and a second surface opposite the first surface, the bone plate having a plate hole that extends therethrough from the first surface to the second surface, the bone plate having a second hardness,
wherein the first and second hardnesses are selected so that a difference therebetween increases a strength of an interface between the bone screw and the bone plate and avoids burring of the threaded head when the bone screw is inserted through the plate hole of the bone plate.

9. The bone fixation system of claim 8, wherein the groove extends along a groove axis perpendicular to a longitudinal axis of the bone screw.

10. The bone fixation system of claim 8, wherein the plate hole is a combination hole.

11. The bone fixation system of claim 8, wherein the plate hole is a variable angle hole.

12. The bone fixation system of claim 8, wherein the second surface of the bone plate comprises a plurality of undercuts.

13. The bone fixation system of claim 8, wherein the plate hole comprises a first tapered portion adjacent the first surface, a second tapered portion adjacent the second surface and a threaded portion extending between the first and second tapered portion.

14. The bone fixation system of claim 8, further comprising a notch adjacent the distal end of the bone screw.

15. The bone fixation system of claim 8, further comprising a recess in a proximal end of the bone screw, the recess configured to engage a driving mechanism.

16. The bone fixation system of claim 8, wherein the shaft is threaded.

17. The bone fixation system of claim 8, wherein a pitch of threads of the shaft is the same as a pitch of the thread of the head.

18. The bone fixation system of claim 8, wherein the plate hole is a variable angle hole including a slot extending along a wall of the hole and configured to interrupt threads thereof.

* * * * *